United States Patent [19]

Caruso et al.

[11] Patent Number: 5,554,770
[45] Date of Patent: Sep. 10, 1996

[54] METHOD FOR MAKING POLYALKYLATED XANTHENES

[75] Inventors: Andrew J. Caruso; Julia L. Lee, both of Schenectady; Joseph A. King, Jr., Niskayuna, all of N.Y.

[73] Assignee: General Electric Company, Schenectady, N.Y.

[21] Appl. No.: 423,662

[22] Filed: Apr. 17, 1995

[51] Int. Cl.$^6$ .................................................. C07D 311/82
[52] U.S. Cl. .................................................. 549/388
[58] Field of Search .............................. 549/388

[56] References Cited

PUBLICATIONS

Baker et al., J. Chem. Soc., 1939, 195–199.
Baker et al., J. Chem. Soc., 1940, 1103–1106.
Baker et al., J. Chem. Soc., 1951, 76–83.

*Primary Examiner*—Nicky Chan
*Attorney, Agent, or Firm*—William H. Pittman

[57] ABSTRACT

Polyalkylated xanthenes are prepared by effecting reaction between an alkylated phenol such as m-cresol and an oxygenated organic material such as acetone in the presence of an acid catalyst such as methanesulfonic acid.

8 Claims, No Drawings

METHOD FOR MAKING POLYALKYLATED XANTHENES

BACKGROUND OF THE INVENTION

The present invention relates to a method for making polyalkylated xanthenes.

Chazan et al., *Bull. Soc. Chim. Fr.*, 1968, 1384, report that condensation of acetone and phenolic material in the presence of phosphorous oxychloride provides a 2.5% yield of tetramethylxanthene. Early observations by Niederl, *Angew. Chem.*, 44, 467 (1931), and Baker et al., *J. Chem. Soc.*, 1939, 195, and *J. Chem. Soc.*, 1951, 76, show that when acetone is exposed to m-cresol in the presence of cold concentrated sulfuric acid, a spirobichroman of the formula

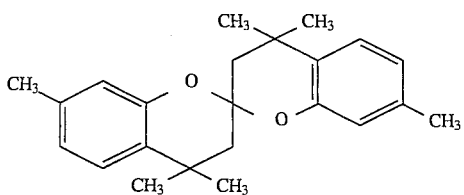

is formed. However, when HCl is used as a catalyst in a mixture of m-cresol and acetone, a chroman of the following formula is formed:

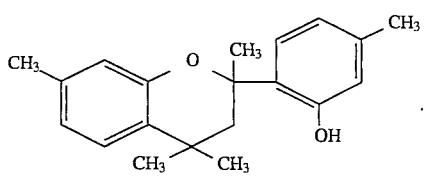

It would be desirable to provide a method for effecting reaction between alkylated phenol and acetone to produce polyalkykated xanthenes at high yields.

It also would be desirable to be able to convert condensation products, such as spirobichromans or chromans, which are formed by reacting acetone and alkylated phenols to polyalkykated xanthenes.

As used hereinafter, the term "alkylated phenol" means a phenol having one or two $C_{1-4}$ alkyl radicals. Among the preferred alkylated phenols, there are included m-cresol, p-cresol and 3,4-dimethylphenol.

SUMMARY OF THE INVENTION

The present invention is based on the discovery that polyalkykated xanthanes can be made in yields exceeding 70% by effecting reaction between acetone and an alkylated phenol in the presence of an acid catalyst, such as methanesulfonic acid, under the reaction conditions set forth below. Unlike the reaction conditions of the prior art, the method of the present invention employs temperatures in the range of about 100°–200° C. It has been further found that polyalkylated xanthenes can be made by a direct reaction between alkylated phenol and at least one of the above shown spirobichroman or chroman condensation products.

The invention is a method for making polyalkylated xanthenes comprising effecting reaction in the presence of an operative amount of a strong acid catalyst and at a temperature in the range of about 100°–200° C. and a pressure in the range of about 1–75 atmospheres, between (A) an oxygenated organic material selected from the class consisting of ketones, spirobichromans and chromans, and (B) an alkylated phenol, the molar ratio of reagent B to reagent A being in the range of about 2–100:1.

DETAILED DESCRIPTION; PREFERRED EMBODIMENT

Some of the polyalkylated xanthenes which can be made by the method of the invention are those having the formula

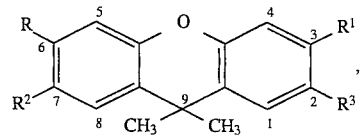

where each of R, $R^1$, $R^2$ and $R^3$ is independently hydrogen or a $C_{1-4}$ alkyl radical, at least two of R–$R^3$ being alkyl. These polyalkykated xanthenes are useful as heat transfer fluids. As shown in copending, commonly owned application Ser. No. 08/218,397, polyalkylated xanthenes also can be converted to polyester intermediates such as xanthene-dicarboxylic acids and their halides and esters. Illustrative poyalkylated xanthenes are 3,6,9,9-tetramethylxanthene, 2,7,9,9-tetramethylxanthene, 2,6,9,9,-tetramethylxanthene and 2,3,6,7,9,9-hexamethylxanthene.

Among the alkylated phenols which may be used as reactants in the method of the present invention, m-and p-cresol are preferred. Some of the dialkyl phenols which can be used are 3,4-dimethylphenol, 3-ethyl-4-methylphenol, 4-ethyl-3-methylphenol, 4-butyl-3-methylphenol and 3-butyl-4-methylphenol. Some of the spirobichromans which can be used are 4,4,4',4',6,6'-hexamethyl-2,2'-spirobichroman, 4,4,4',4',7,7'-hexamethyl-2,2'-spirobichroman, 4,4,4',4',6,7'-hexamethyl-2,2'-spirobichroman and 4,4,4',4',6,6',7,7'-octamethyl-2,2'-spirobichroman. Chromans which can be used include 2'-(2-hydroxy-4-methylphenyl)-2',4',4',7'-tetramethylchroman, 2'-(2-hydroxy-5-methylphenyl)-2',4',4',7'-tetramethylchroman, 2'-(2-hydroxy-5-methylphenyl)-2',4',4',6'-tetramethylchroman, 2'-(2-hydroxy-4-methylphenyl)-2',4',4',6'-tetramethylchroman, 2'-(2-hydroxy-4,5-dimethylphenyl)-2',4',4',7'-tetramethylchroman, and 2'-(2-hydroxy-4,5-methylphenyl)-2',4',4',6',7'-pentamethylchroman.

In the practice of the invention, reaction is effected in the presence of a strong acid catalyst between an alkylated phenol and an oxygenated organic material, which hereinafter is intended to mean acetone unless a spirobichroman or chroman is specifically designated.

Suitable strong acid catalysts are acids having a pKa in the range from about −12 to about 1. There are included organic sulfonic acids such as methanesulfonic acid, p-toluenesulfonic acid, camphorsulfonic acid and various aromatic resin-bound sulfonic acids as exemplified by Nafion® ion exchange beads. An effective amount of acid catalyst is about 0.1–50% by weight based on the total weight of the reaction mixture. The reaction can be conducted or at pressures in the range of about 1–75 atmospheres, under sealed conditions if desired.

Recovery of the polyalkylated xanthenes can be facilitated by allowing the reaction mixture to cool and then diluting it with a suitable inert organic solvent such as toluene, ethyl acetate or methylene dichloride. The organic layer can be separated and washed with an aqueous basic solution, such as a solution of NaOH or $NaHCO_3$. The organic layer can then be dried, for example with anhydrous $MgSO_4$, and concentrated under reduced pressure.

The method of the invention is illustrated by the following examples.

EXAMPLE 1

A mixture of 2 mL (19.1 mmol) of m-cresol, 172 mg (2.96 mmol) of acetone, and 16.8 mg (0.17 mmol) of methanesulfonic acid was heated under sealed conditions at 150° C. for 21 hours. The mixture was assayed by quantitative gas chromatography using tetradecane as an internal standard. There was obtained 514 mg (73% yield) of 3,6,9,9-tetramethylxanthene and 17 mg of 4,4,4'4'7,7'-hexamethyl-2,2'-spirobichroman.

EXAMPLE 2

There was heated for 22 hours at 145°–150° C., under sealed conditions, a mixture of 52.1 mg (0.155 mmol) of the product of Example 1 and 2.0 mL of a solution of methanesulfonic acid in m-cresol (19 mg/mL). The mixture was allowed to cool and transferred to a container 100.0 mg of tetradecane in 10 mL of ethyl acetate. It was diluted to 100 mL with additional ethyl acetate. Gas chromatography showed a yield of 101.5 mg (92%) of 3,6,9,9,-tetramethylxanthene.

EXAMPLE 3

A mixture of 2 mL (19.1 mmol) of p-cresol, 151.8 mg (2.61 mmol) of acetone, and 21.5 mg (0.22 mmol) of methanesulfonic acid was heated for 26 hours at 150° C. under sealed conditions. It was assayed in accordance with the procedure of Example 1. There was obtained 255 mg (41% yield) of 2,7,9,9-tetramethylxanthene and 53 mg (18%) of 4,4,4'4'6'6'-hexamethyl-2,2,-spirochroman.

EXAMPLE 4

A mixture of 2.126 g (17.4 mmol) of 3,4-dimethylphenol, 98 mg (1.69 mmol) of acetone, and 20.9 mg (0.22 mmol) of methanesulfonic acid was heated for 62 hours at 100° C. and then at 150° C. for 26 hours. The mixture was allowed to cool, diluted with 30 mL of toluene, and washed three times with a 10% aqueous NaOH solution, water and brine. The organic layer was dried over $MgSO_4$ and then concentrated under reduced pressure. There was obtained 335 mg of crude 2,3,6,7,9,9-hexamethylxanthene as a tan solid.

EXAMPLE 5

A mixture of 32.40 g (299.6 mmol) of m-cresol, 19.18 g (330.2 mmol) of acetone, and 2.00 g (20.8 mmol) of methanesulfonic acid was heated with stirring at 100° C. for 54 hours. After cooling, the mixture was diluted with 100 mL of toluene and washed several times with saturated aqueous $NaHCO_3$ and water. Following the procedure of Example 4, there was obtained 29.13 g of a dark oil which was shown to be a mixture of 2'-(2-hydroxy-4-methyl)-2', 4',4',7'-tetramethylchroman, 4,4,4',4',7,7'- hexamethyl-2,2'-spirobichroman and 3,6,6,9-tetramethylxanthene. A portion of the 2'-(2-hydroxy-4-methyl)-2',4',4',7'-tetramethylchroman was recovered by column chromatography as a glassy solid.

EXAMPLE 6

A mixture of 100 mg (0.34 mmol) of 2'-(2'-hydroxy-4-methylphenyl)-2',4',4',7'-tetramethylchroman, 2.0 mL of m-cresol, 23.9 mg of methanesulfonic acid, and 100.7 mg of tetradecane as an internal standard was heated under sealed conditions at 150° C. for 21.5 hours. Based on the above-described gas chromatographic and workup procedures, there was obtained about a 90% yield of crude 3,6,9,9-tetramethylxanthene.

What is claimed is:

1. A method for making polyalkylated xanthenes comprising effecting reaction in the presence of an operative amount of an organic sulfonic acid as catalyst and at a temperature in the range of about 100°–200° C. and a pressure in the range of about 1–75 atmospheres, between (A) an oxygenated organic material selected from the class consisting of ketones, spirobichromans and chromans, and (B) an alkylated phenol, the molar ratio of reagent B to reagent A being in the range of about 2–100:1.

2. A method in accordance with claim 1 where the oxygenated organic material is acetone.

3. A method in accordance with claim 1 where the oxygenated organic material is a spirobichroman.

4. A method in accordance with claim 1 where the oxygenated organic material is a chroman.

5. A method in accordance with claim 1 where the alkylated phenol is m-cresol.

6. A method in accordance with claim 1 where the alkylated phenol is p-cresol.

7. A method in accordance with claim 1 where the alkylated phenol is 3,4-dimethylphenol.

8. A method n accordance with claim 1 wherein the catalyst is methanesulfonic acid.

* * * * *